United States Patent
Choi et al.

(10) Patent No.: US 10,039,687 B2
(45) Date of Patent: Aug. 7, 2018

(54) DRIVING MODULES AND MOTION ASSISTANCE APPARATUSES INCLUDING THE SAME

(71) Applicant: Samsung Electronics Co., Ltd., Suwon-si, Gyeonggi-do (KR)

(72) Inventors: Hyun Do Choi, Yongin-si (KR); Taesin Ha, Seongnam-si (KR); Jeong Hun Kim, Suwon-si (KR); Se-Gon Roh, Suwon-si (KR); Min Hyung Lee, Seoul (KR); Youn Baek Lee, Yongin-si (KR); Jong Won Lee, Suwon-si (KR); Byung June Choi, Gunpo-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 903 days.

(21) Appl. No.: 14/531,001

(22) Filed: Nov. 3, 2014

(65) Prior Publication Data
US 2015/0335514 A1 Nov. 26, 2015

(30) Foreign Application Priority Data
May 23, 2014 (KR) ........................ 10-2014-0062277

(51) Int. Cl.
*A61H 3/00* (2006.01)
*A61F 2/60* (2006.01)
*A61H 1/02* (2006.01)
*A61F 5/01* (2006.01)

(52) U.S. Cl.
CPC .............. *A61H 3/00* (2013.01); *A61F 2/605* (2013.01); *A61H 1/0244* (2013.01);
(Continued)

(58) Field of Classification Search
CPC ........ A61H 1/02; A61H 1/0237; A61H 1/024; A61H 1/0244; A61H 1/0262;
(Continued)

(56) References Cited

U.S. PATENT DOCUMENTS 7,963,932 B2 * 6/2011 Ashihara ............... A61F 5/0102
601/35
8,303,525 B2 11/2012 Ikeuchi et al.
(Continued)

FOREIGN PATENT DOCUMENTS

JP 2008278921 A 11/2008
JP 4332136 B2 9/2009
(Continued)

*Primary Examiner* — Justine Yu
*Assistant Examiner* — Colin W Stuart
(74) *Attorney, Agent, or Firm* — Harness, Dickey & Pierce, P.L.C.

(57) ABSTRACT

A driving module may include: an object fix member configured to be fixed to an object; a first sub-module including a body portion, connected to a first side of the object fix member, and a first rotating member, connected rotatably to the body portion; a second sub-module including an extension link, connected to a second side of the object fix member, and a second rotating member, connected rotatably to the extension link; and/or a power transmitting member connected to the first rotating member and the second rotating member, and configured to transmit power.

17 Claims, 13 Drawing Sheets

(52) U.S. Cl.
CPC .......... *A61H 1/0262* (2013.01); *A61F 5/0102* (2013.01); *A61F 2005/0155* (2013.01); *A61H 1/02* (2013.01); *A61H 1/0237* (2013.01); *A61H 2003/007* (2013.01); *A61H 2201/149* (2013.01); *A61H 2201/1436* (2013.01); *A61H 2201/164* (2013.01); *A61H 2201/165* (2013.01); *A61H 2201/1628* (2013.01); *A61H 2201/5064* (2013.01); *A61H 2201/5069* (2013.01)

(58) Field of Classification Search
CPC ........ A61H 1/0274; A61H 1/001; A61H 3/00; A61H 2003/002; A61H 2003/007; A61F 2/605
USPC .......................................... 601/5, 33, 34, 35
See application file for complete search history.

(56) References Cited

U.S. PATENT DOCUMENTS

| | | | |
|---|---|---|---|
| 2004/0116839 A1* | 6/2004 | Sarkodie-Gyan | A61H 3/008 601/35 |
| 2006/0070461 A1* | 4/2006 | Delair | G01M 13/027 73/862.325 |
| 2009/0292369 A1* | 11/2009 | Kazerooni | B25J 9/0006 623/27 |
| 2010/0036302 A1* | 2/2010 | Shimada | A61F 5/0102 602/16 |
| 2010/0298746 A1* | 11/2010 | Shimizu | A61H 3/008 601/35 |
| 2011/0172570 A1 | 7/2011 | Shimizu et al. | |
| 2011/0214524 A1 | 9/2011 | Jacobsen et al. | |
| 2013/0138020 A1 | 5/2013 | Yasuhara | |
| 2014/0276265 A1* | 9/2014 | Caires | A61H 3/00 601/34 |
| 2014/0330431 A1* | 11/2014 | Hollander | B25J 9/0006 700/245 |

FOREIGN PATENT DOCUMENTS

| | | |
|---|---|---|
| JP | 4573989 B2 | 11/2010 |
| JP | 5021574 B2 | 9/2012 |
| JP | 2012192013 A | 10/2012 |
| KR | 100731899 B1 | 6/2007 |
| KR | 2013011763 A | 10/2013 |

* cited by examiner

DRIVING MODULES AND MOTION ASSISTANCE APPARATUSES INCLUDING THE SAME

CROSS-REFERENCE TO RELATED APPLICATION(S)

This application claims priority from Korean Patent Application No. 10-2014-0062277, filed on May 23, 2014, in the Korean Intellectual Property Office (KIPO), the entire contents of which are incorporated herein by reference.

BACKGROUND

1. Field

Some example embodiments may relate generally to driving modules. Some example embodiments may relate generally to motion assistance apparatuses including the same.

2. Description of Related Art

With the onset of rapidly aging societies, a number of people may experience inconvenience and/or agony from joint problems, and interest in motion assistance apparatuses that may enable the elderly or patients with joint problems to walk with less effort is growing. In addition, motion assistance apparatuses that may increase muscular strength of human bodies may be in development for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and pedial frames disposed on feet of the users. The pelvic frames and the femoral frames may be connected rotatably by hip joint portions, the femoral frames and the sural frames may be connected rotatably by knee joint portions, and the sural frames and the pedial frames may be connected rotatably by ankle joint portions.

The motion assistance apparatuses may include active joint structures including hydraulic systems and/or driving motors to drive each joint portion to improve muscular strength of legs of the users. For example, motors to transmit driving power may be attached to the hip joint portions and/or the knee joint portions, respectively.

The users may wear the motion assistance apparatuses over the users' clothing.

In general, driving modules and motion assistance apparatuses may include lower extremity muscular strength assistance robots for behavior of lower extremities. These driving modules and motion assistance apparatuses may serve to assist force of wearer's legs to assist walking using human-robot synchronization.

Such driving modules and motion assistance apparatuses may be driven so as to sense a wearer's intention to walk and to assist corresponding muscular strength. Here, sensing of the wearer's intention to walk may mean sensing of a wearer's intention to start walk or to finish walk, or mean sensing of moving states of the left foot and the right foot.

Although some example embodiments will be described with relation to driving modules and motion assistance apparatuses for humans, those skilled in the art will appreciate that some example embodiments may be applied to other types of modules, apparatuses, and systems, such as driving modules and motion assistance apparatuses for animals, or more general purpose systems.

SUMMARY

In some example embodiments, a driving module may comprise: an object fix member configured to be fixed to an object; a first sub-module comprising a body portion, connected to a first side of the object fix member, and a first rotating member, connected rotatably to the body portion; a second sub-module comprising an extension link, connected to a second side of the object fix member, and a second rotating member, connected rotatably to the extension link; and/or a power transmitting member connected to the first rotating member and the second rotating member, and configured to transmit power.

In some example embodiments, the first rotating member and the second rotating member may be on opposite sides based on the object fix member.

In some example embodiments, the first sub-module may further comprise: a pivot between the body portion and the object fix member configured to connect the body portion movably to the object fix member.

In some example embodiments, the pivot may comprise a pivot axis configured to enable the body portion to be rotatable with respect to the object fix member.

In some example embodiments, the driving module may further comprise: a restoring spring on a first side of the pivot, configured to return the body portion to a standard position when an external force applied to the body portion is removed.

In some example embodiments, the pivot may comprise flexible material.

In some example embodiments, the pivot may comprise flexible material having elasticity.

In some example embodiments, a first side of the extension link may be connected to the object fix member. A second side of the extension link may extend to a joint part of the object. The second rotating member may be on the second side of the extension link.

In some example embodiments, an axis of rotation of the second rotating member may be orthogonal to the pivot axis of the pivot.

In some example embodiments, the power transmitting member may be in a direction orthogonal to the pivot axis of the pivot and an axis of rotation of the first rotating member.

In some example embodiments, the power transmitting member may comprise a flat spring.

In some example embodiments, the power transmitting member may be a flat spring.

In some example embodiments, the power transmitting member may comprise: a first power transmitting member configured to connect a first side of the first rotating member to a first side of the second rotating member; and/or a second power transmitting member configured to connect a second side of the first rotating member to a second side of the second rotating member. The first and second sides of the first rotating member are on opposite sides based on an axis of rotation of the first rotating member. The first and second sides of the second rotating member are on opposite sides based on an axis of rotation of the second rotating member.

In some example embodiments, the second sub-module may further comprise: a connection axis on a first side of the second rotating member and in a direction intersecting a direction of an axis of rotation of the second rotating member.

In some example embodiments, the driving module may further comprise: a case configured to prevent external exposure of at least a portion of the power transmitting member.

In some example embodiments, the case may comprise a holding portion configured to hold clothes.

In some example embodiments, a motion assistance apparatus may comprise: an actuator module configured to provide power; a driving module comprising a first sub-module configured to receive the power from the actuator module, a second sub-module configured to receive the power from the first sub-module, and a power transmitting member configured to transmit the power between the first sub-module and the second sub-module; and/or a supporting module connected to the second sub-module and configured to support and move a part of an object. The second sub-module may be on a first side of a joint part connected to the part of the object. The first sub-module may be spaced away from the joint part.

In some example embodiments, the motion assistance may further comprise: a connection module between the driving module and the supporting module. The connection module may comprise: a first connection link; and/or a second connection link connected movably to the first connection link, and configured to adjust an overall length of the connection module.

In some example embodiments, a motion assistance apparatus may comprise: a power providing module comprising a driving source configured to generate power; a power applying module comprising a rotating member on a first side of a joint part of an object, configured to supplement or be substituted for a function of the joint part, and a supporting module connected to the rotating member and configured to support a portion of the rotating member connected to the joint part; a power transmitting member configured to transmit the power from the power providing module to the rotating member; and/or a case configured to cover at least a portion of the power transmitting member.

In some example embodiments, the rotating member may be on a first side of a hip joint of the object. The supporting module may be configured to support a lower body of the object. The power providing module may be on an upper body of the object. The case may be on a waist of the object.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
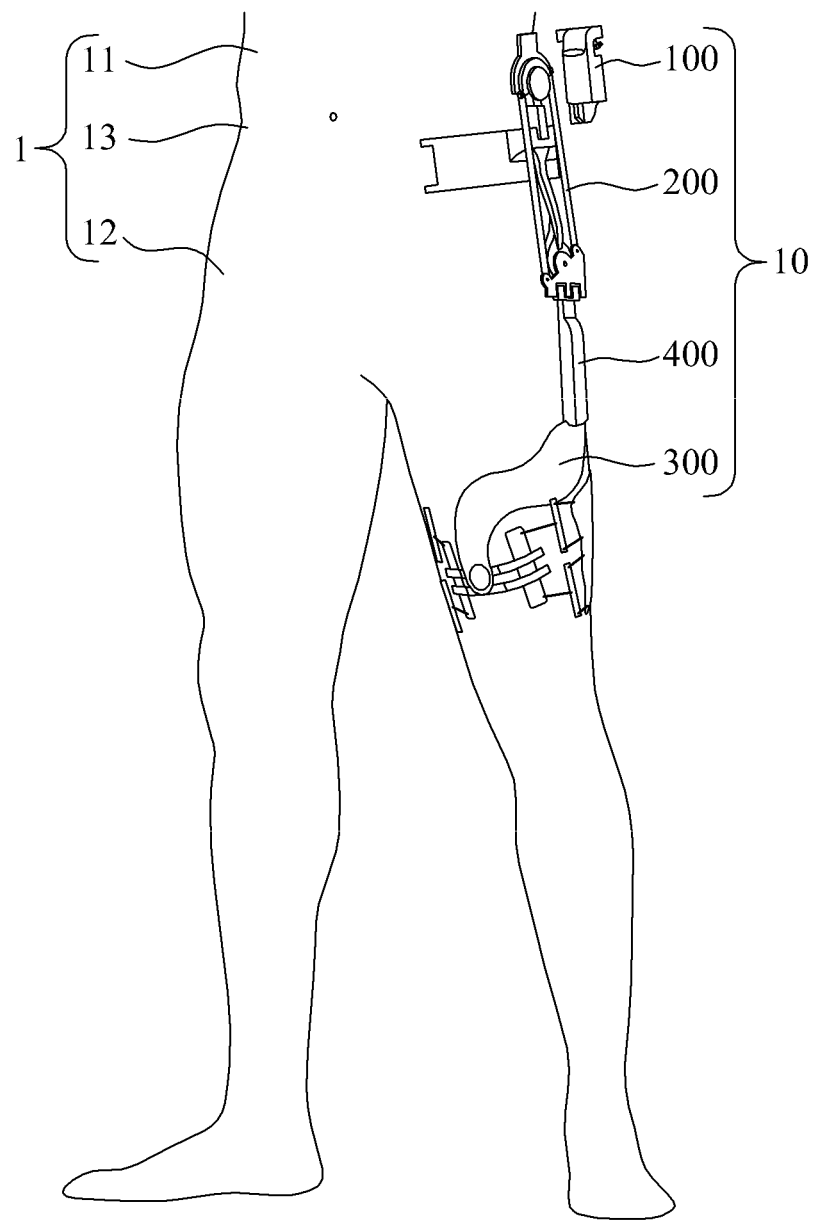
FIG. 1 illustrates a motion assistance apparatus disposed on an object according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIG. 1 illustrates a motion assistance apparatus 10 disposed on an object 1 according to some example embodiments.

Referring to FIG. 1, the motion assistance apparatus 10 may be worn on the object 1 to assist a motion of the object 1. The object 1 may include a first part 11 on which a power providing module is disposed, a second part 12 on which a power applying module is disposed, and a third part 13 to support the power providing module and the power applying module. For example, the first part 11 may correspond to an upper body, the second part 12 may corresponds to a lower body, and the third part 13 may correspond to a waist.

The power providing module refers to a module including a driving source that generates power. The power applying module refers to a module including a rotating member to supplement or be substituted for a function of a portion of an object, for example, a joint part. The power applying module may be disposed on one side of the joint part.

By disposing the power providing module and the power applying module to be spaced apart from each other, a volume of a product to be disposed on the joint part may be reduced.

Although FIG. 1 illustrates a case in which the object 1 corresponds to a human, the object 1 may also correspond to an animal or a robot. However, the object 1 is not limited thereto. In addition, although FIG. 1 illustrates a case in which the motion assistance apparatus 10 assists a motion of a thigh of the object 1, the motion assistance apparatus 10 may also assist a motion of another part of an upper body, for example, a hand, an upper arm, and a lower arm of the object 1, or a motion of another part of a lower body, for example, a foot and a calf of the object 1. The motion assistance apparatus 10 may assist a motion of a part of the object 1.

Hereinafter, a case in which the motion assistance apparatus 10 assists a motion of a thigh of a human will be described.

The motion assistance apparatus 10 may include an actuator module 100, a driving module 200, a supporting module 300, and a connection module 400.

The actuator module 100 may provide power to drive the motion assistance apparatus 10. The actuator module 100 may be coupled to the driving module 200 to transmit the power to the driving module 200.

The actuator module 100 may be provided to be detachable from the driving module 200. FIG. 1 illustrates the actuator module 100 detached from the driving module 200.

The actuator module 100 may include, for example, a motor to receive voltage or current and generate power, or a hydraulic pump. However, a type of the actuator module 100 is not limited to the foregoing example embodiments.

The actuator module 100 may include a motor, a gear connected to the motor to transmit driving power to the driving module 200, and a position sensor to sense an angle of rotation of the gear.

The driving module 200 may receive the power from the actuator module 100 and transmit the power to the supporting module 300. The driving module 200 will be described in detail later.

The supporting module 300 may support a portion of which a motion is to be assisted using the motion assistance apparatus 10. The supporting module 300 may transmit a force to a portion of the object 1 using the power received from the driving module 200.

The supporting module 300 may support a portion of the lower body of the object 1. The supporting module 300 may support a thigh of the object 1. The supporting module 300 may transmit the power received from the driving module 200 to the lower body of the object 1, thereby moving the lower body of the object 1.

The connection module 400 may be interposed between the driving module 200 and the supporting module 300. The connection module 400 may connect the driving module 200 to the supporting module 300. However, the connection module 400 may not be necessarily provided, and the driving module 200 may be connected directly to the supporting module 300. In some example embodiments, descriptions on the connection module 400 may be applicable to the supporting module 300.

Figure 2:
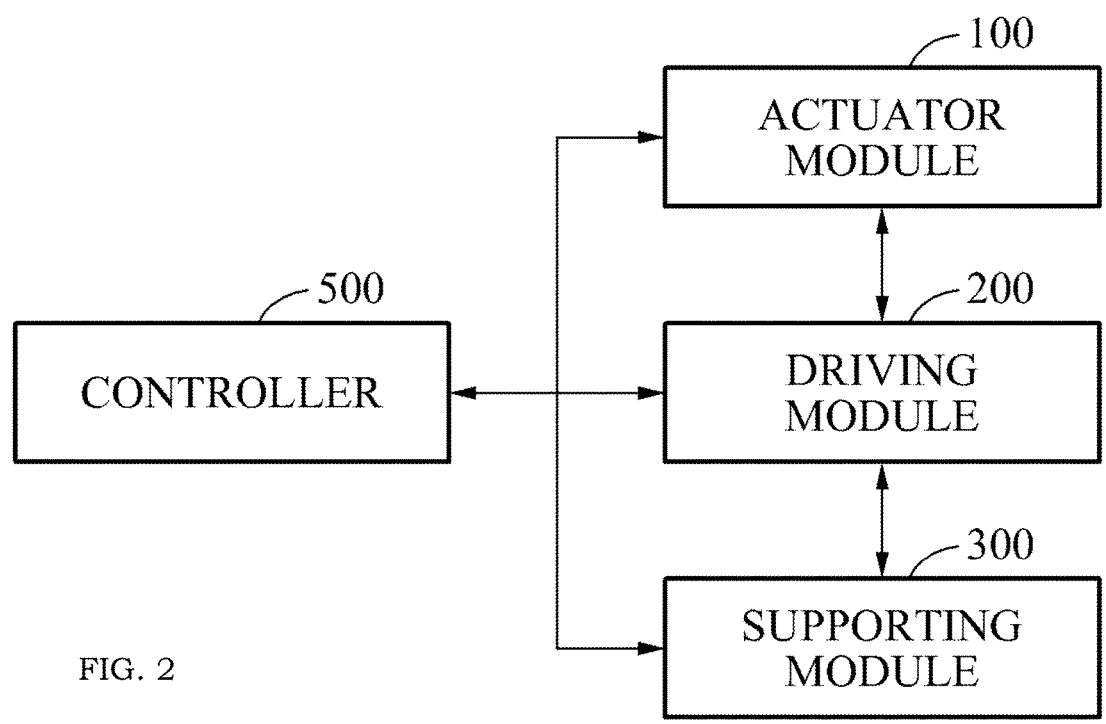
FIG. 2 is a block diagram illustrating a motion assistance apparatus according to some example embodiments.

FIG. 2 is a block diagram illustrating the motion assistance apparatus 10.

Referring to FIG. 2, the motion assistance apparatus 10 may further include a controller 500 to control the actuator module 100, the driving module 200, and the supporting module 300.

The controller 500 may be mechanically or electrically connected to the actuator module 100. The controller 500 may turn the actuator module 100 on or off. The controller 500 may adjust an output of the actuator module 100. The controller may adjust a magnitude, a velocity, or a direction of the power provided by the actuator module 100.

When the actuator module 100 corresponds to a motor, the controller 500 may control a torque, a velocity of rotation, a direction of rotation, or an angle of rotation of the motor.

When the actuator module 100 includes a position sensor, the controller 500 may control the actuator module 100 based on a signal transferred from the position sensor.

The controller 500 may also control the actuator module 100 based on a signal transferred from a position sensor belonging to the driving module 200 or a position sensor belonging to the supporting module 300.

Although FIG. 2 illustrates the controller 500 being connected directly to the actuator module 100, the driving module 200, and the supporting module 300, example embodiments are not limited thereto.

Figure 3:
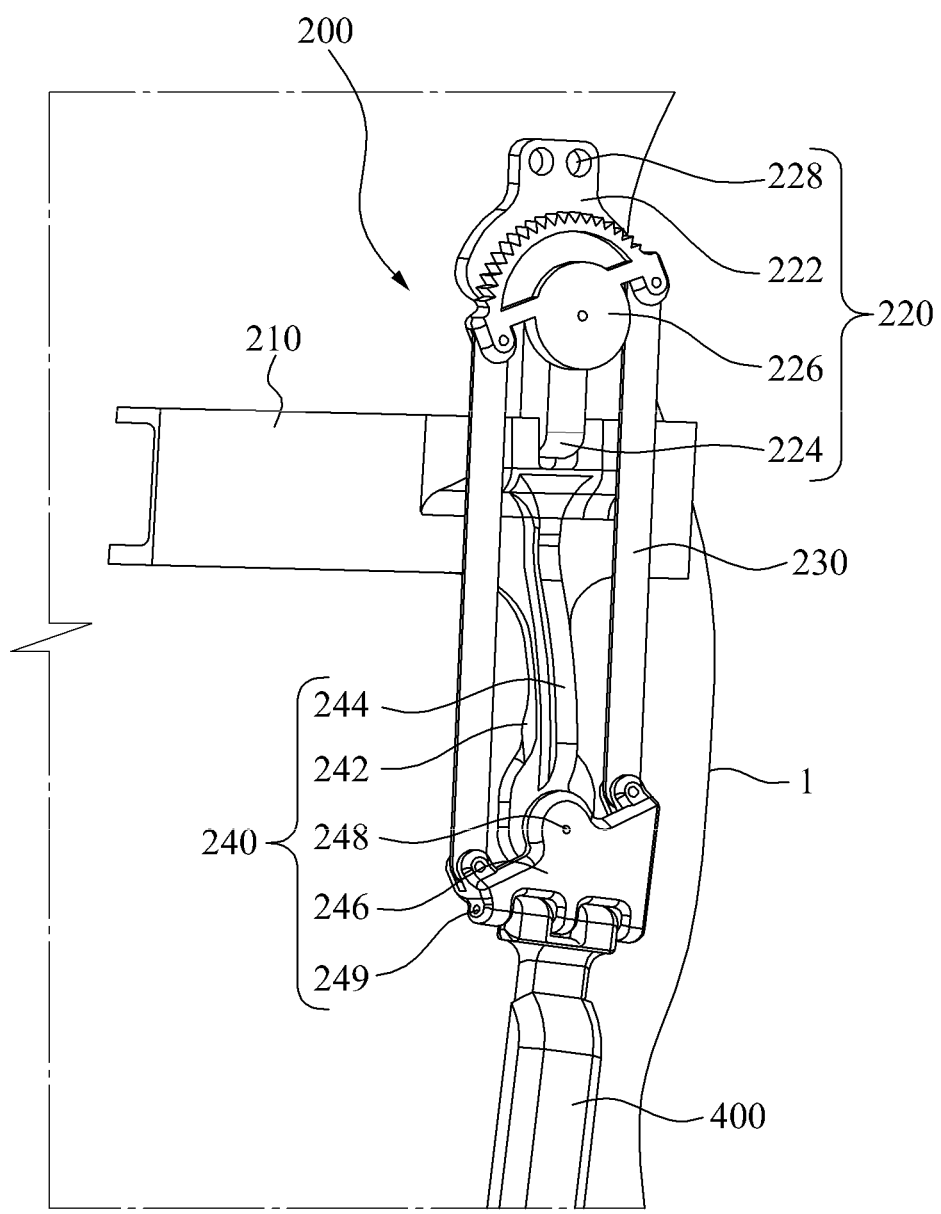
FIG. 3 illustrates a driving module and a connection module according to some example embodiments.

FIG. 3 illustrates the driving module 200 and the connection module 400.

Referring to FIG. 3, the driving module 200 may include an object fix member 210, a first sub-module 220, a power transmitting member 230, and a second sub-module 240.

The object fix member 210 may fix the driving module 200 to the object 1. The object fix member 210 may be in contact with at least a portion of an outer surface of the object 1. The object fix member 210 may be provided in a form of covering the outer surface of the object 1. The object fix member 210 may be formed to be curved in a form corresponding to a contact portion of the object 1. The object fix member 210 may include a curved surface to be in contact with the object 1.

The object fix member 210 may be fixed on one side of the third part 13 of the object 1. The object fix member 210 may be fixed to the first part 11 of the object 1. The object fix member 210 may be fixed on an opposite side of the second part 12 of the object 1 based on the third part 13 of the object 1.

The first sub-module 220 may transmit the power received from the actuator module 100 to the second sub-module 240. The first sub-module 220 may include a body portion 222, a pivot 224, a first rotating member 226, and a fastening portion 228.

The body portion 222 may be connected to the object fix member 210. The body portion 222 may be connected movably to the object fix member 210. The body portion 222 may be provided on one side of the object fix member 210.

For example, the body portion 222 may be provided on an upper side of the object fix member 210. The body portion 222 may be disposed to be biased toward the first part 11 of the object 1.

The pivot 224 may be provided on one side of the body portion 222, and connected to the object fix member 210. The pivot 224 may be provided between the body portion 222 and the object fix member 210. The pivot 224 may be provided movably with respect to the object fix member 210.

In some example embodiments, the pivot 224 may include a hinge. The pivot 224 may rotate in one direction with respect to the object fix member 210. The pivot 224 may rotate in a direction intersecting a longitudinal direction of the object fix member 210. For example, the pivot 224 may rotate in a direction orthogonal to the longitudinal direction of the object fix member 210.

In some example embodiments, the pivot 224 may include a flexible material. The flexible material may be formed using an elastic material. In some example embodiments, the body portion 222 may move in free directions on the pivot 224 with respect to the object fix member 210. In addition, when an external force is eliminated, the body portion 222 may return to a standard position corresponding to an original position.

In some example embodiments, the pivot 224 may include a ball joint. In some example embodiments, the body portion 222 may move in free directions on the pivot 224 with respect to the object fix member 210.

The first rotating member 226 may be provided rotatably with respect to the body portion 222. The first rotating member 226 may include a gear to be engaged with the gear of the actuator module 100. An axis of rotation of the first rotating member 226 may be disposed to be orthogonal to a pivot axis of the pivot 224.

The fastening portion 228 may be fastened to the actuator module 100. The fastening portion 228 may be provided on one side of the body portion 222. For example, the fastening portion 228 and the actuator module 100 may be provided in a fastening structure of a protrusion and a hole, a structure of a hook and a recess, or a structure of being coupled by a separate fastening member. However, a fastening structure of the fastening portion 228 and the actuator module 100 is not limited thereto.

The fastening portion 228 may be provided detachably from the actuator module 100. When the fastening portion 228 is fastened to the actuator module 100, the first rotating member 226 may be prepared to receive the power transmitted from the actuator module 100. When the fastening portion 228 is detached from the actuator module 100, the transmission of the power from the actuator module 100 and the first rotating member 226 may be blocked.

The power transmitting member 230 may transmit the power from the first sub-module 220 to the second sub-module 240. One side of the power transmitting member 230 may be connected to the first rotating member 226, and another side of the power transmitting member 230 may be connected to the second sub-module 240. The power transmitting member 230 may transmit the power using a pushing or pulling force, a friction force, a tensile force, or an elastic force.

The power transmitting member 230 may extend to both sides based on the object fix member 210. For example, the power transmitting member 230 may extend in a direction intersecting the longitudinal direction of the object fix member 210. The power transmitting member 230 may be disposed in a direction perpendicular to the longitudinal direction of the object fix member 210. The power transmitting member 230 may be disposed in a direction perpendicular to the pivot axis of the pivot 224.

The power transmitting member 230 may include a longitudinal direction member disposed in a longitudinal direction between the first rotating member 226 and the second sub-module 240. For example, the longitudinal direction member may include a wire, a cable, a string, a link, a rubber band, a spring, a belt, and a chain. The spring may include a coil spring or a flat spring. The longitudinal direction member may include an elastic member having elasticity. The power transmitting member 230 may be configured using a combination of at least two types of longitudinal direction members.

The power transmitting member 230 may be connected rotatably to the first rotating member 226 and the second sub-module 240.

The power transmitting member 230 may include a first power transmitting member to connect one side of the first rotating member 226 to one side of the second sub-module 240, and a second power transmitting member to connect another side of the first rotating member 226 to another side of the second sub-module 240. The first power transmitting member and the second power transmitting member may be disposed on opposite sides based on the axis of rotation of the first rotating member 226. The first power transmitting member and the second power transmitting member may be disposed to be parallel to each other.

Although FIG. 3 illustrates two power transmitting members 230, a single power transmitting member 230 or at least three power transmitting members 230 may be provided.

In some example embodiments, when a single power transmitting member 230 is provided, the power transmitting member 230 may correspond to a longitudinal direction member provided in a form of a doughnut covering both the first rotating member 226 and a second rotating member 246. The power transmitting member 230 may correspond to, for example, a belt or a chain.

In some example embodiments, when a single power transmitting member 230 is provided, the power transmitting member 230 may correspond to a flexible material or a rigid body formed in a longitudinal direction. The power transmitting member 230 may correspond to, for example, a flat spring.

The second sub-module 240 may receive the power transmitted from the first sub-module 220 through the power transmitting member 230, and transmit the received power to the object 1. The second sub-module 240 may drive the supporting module 300 of FIG. 1. The second sub-module 240 may be connected to the supporting module 300 through the connection module 400.

The second sub-module 240 may include an extension link 242, a reinforcing rib 244, the second rotating member 246, and a connection axis 249.

The extension link 242 may be connected to the object fix member 210. The extension link 242 may be fixed to the object fix member 210. The extension link 242 may be formed to be integrated with the object fix member 210. The extension link 242 may be connected to another side of the object fix member 210. The extension link 242 may be disposed on an opposite side of the body portion 222. The extension link 242 may extend from the object fix member to the opposite side of the body portion 222.

For example, one side of the extension link 242 may be connected to the object fix member 210, and another side of the extension link 242 may extend to a joint part. The other side of the extension link 242 may be disposed at a height at which the joint part of the object 1 is positioned from a ground. The extension link 242 may have a curved inner side surface corresponding to a shape of a human pelvis.

The extension link 242 may be disposed in a direction parallel to the power transmitting member 230. The extension link 242 may be disposed in a direction perpendicular to the pivot axis of the pivot 224.

The reinforcing rib 244 may reinforce a rigidity of the extension link 242. The reinforcing rib 244 may be provided on one side of the extension link 242. The reinforcing rib 244 may be disposed in a direction in which the extension link 242 is disposed. The reinforcing rib 244 may be disposed in a direction parallel to the power transmitting member 230. The extension link 242 may be disposed in a direction perpendicular to the pivot axis of the pivot 224.

The second rotating member 246 may be provided rotatably with respect to the extension link 242. The second rotating member 246 may be connected to the power transmitting member 230. One side of the second rotating member 246 may be connected to the first power transmitting member, and another side of the second rotating member 246 may be connected to the second power transmitting member. The first power transmitting member and the second power transmitting member may be connected in opposite directions based on an axis of rotation of the second rotating member 246.

The second rotating member 246 may rotate through interoperation with a rotary motion of the first rotating member 226. The second rotating member 246 may supplement or substitute for a function of a joint part of the object 1. For example, the second rotating member 246 may supplement or be substituted for a function of a hip joint of the object 1.

The second rotating member 246 may be disposed on one side of the joint part of the object 1. In some example embodiments, the second rotating member 246 may transmit a driving power in a direction matching a motion direction of the joint part.

An axis of rotation 248 of the second rotating member 246 may be disposed in a direction identical to the axis of rotation of the first rotating member 226. The axis of rotation 248 of the second rotating member 246 may be perpendicular to the pivot axis of the pivot 224.

The connection axis 249 may be interposed between the second rotating member 246 and the connection module 400. The connection axis 249 may enable the connection module 400 to be movable with respect to the second rotating member 246.

The axis of rotation 248 and the connection axis 249 may be disposed in different directions. The connection module 400 may perform a two degree of freedom motion by means of the axis of rotation 248 and the connection axis 249.

The connection module 400 may be provided movably with respect to the second rotating member 246. For example, the connection module 400 may rotate on the connection axis 249. The connection module 400 may perform a two degree of freedom motion with respect to the object fix member 210 by means of the axis of rotation 248 and the connection axis 249.

A separate axis may be added to the connection module 400 or the second sub-module 240. In some example embodiments, the separate axis may have a direction differing from directions of the axis of rotation 248 and the connection axis 249. In some example embodiments, the connection module 400 may be provided to perform a three or more degree of freedom motion with respect to the object fix member 210.

Figure 4:
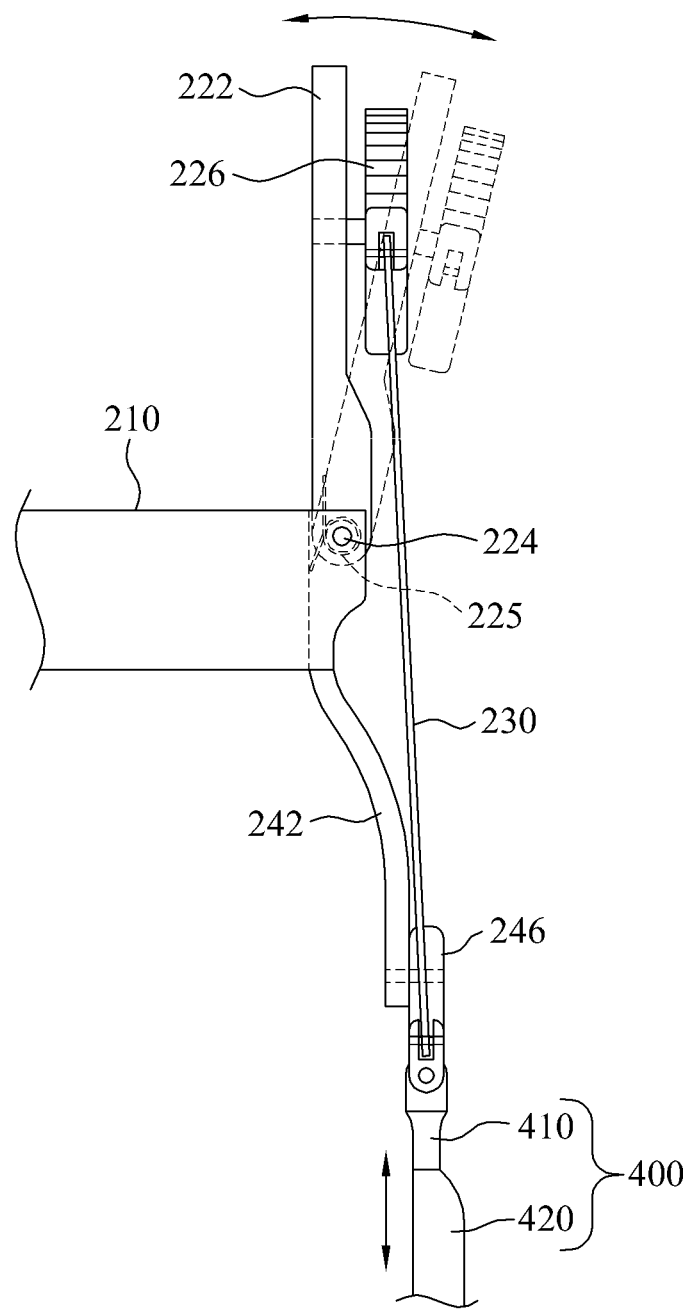
FIG. 4 is a front view illustrating a driving module and a connection module according to some example embodiments.

FIG. 4 is a front view illustrating the driving module 200 and the connection module 400. In FIG. 4, the power transmitting member 230 of FIG. 3 is omitted.

Referring to FIG. 4, the body portion 222 of the driving module 200 may rotate with respect to the object fix member 210. The body portion 222 may rotate in response to a lateral movement of the first part 11 the object 1, and may not restrain a lateral movement of the first part 11 of the object 1.

The driving module 200 may further include a restoring spring 225.

The restoring spring 225 may apply a restoring force to return the body portion 222 to a standard position. The restoring spring 225 may be provided on one side of the pivot 224. For example, the restoring spring 225 may correspond to a torsion spring.

When the power transmitting member 230 of FIG. 3 corresponds to a flat spring, the body portion 222 may return to the standard position by an elastic force of the flat spring. When the body portion 222 rotates by an external force received in response to a movement of the object 1, the flat spring may transmit power while being bent based on a magnitude of the external force. In some example embodiments, the power may be transmitted while preventing excessive buckling.

A length of the connection module 400 may vary. The length of the connection module 400 may be adjusted to be suitable for a condition of the object 1. The connection module 400 may include a first connection link 410 and a second connection link 420.

The first connection link 410 may be connected to the second rotating member 246.

The second connection link 420 may be connected movably to the first connection link 410. The overall length of the connection module 400 may vary depending on relative motions of the second connection link 420 and the first connection link 410. The supporting module 300 may perform a three degree of freedom motion by means of the connection module 400, the axis of rotation 248, and the connection axis 249.

For example, the second connection link 420 may be connected slidingly with respect to the first connection link 410. However, a connection scheme for the first connection link 410 and the second connection link 420 is not limited to a sliding scheme. Any connection method that may vary the overall length of the connection module 400 may be used.

Figure 5:
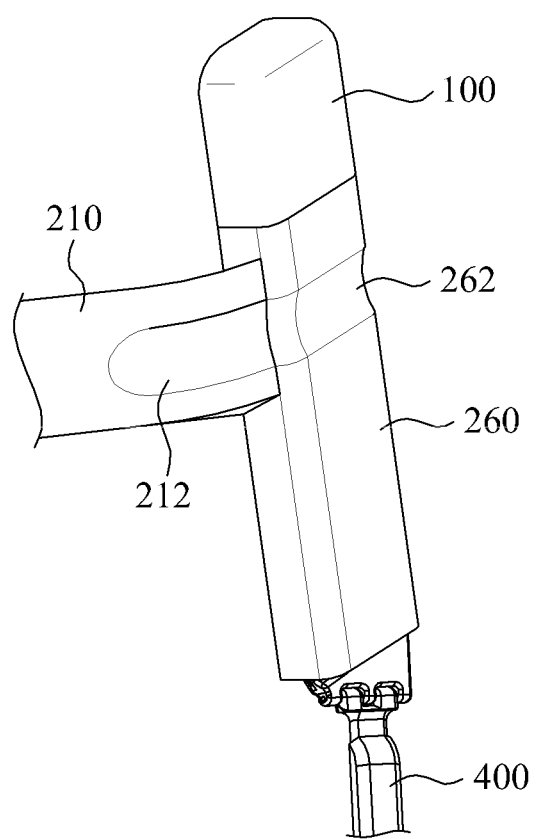
FIG. 5 illustrates a motion assistance apparatus including a case according to some example embodiments.
Figure 6:
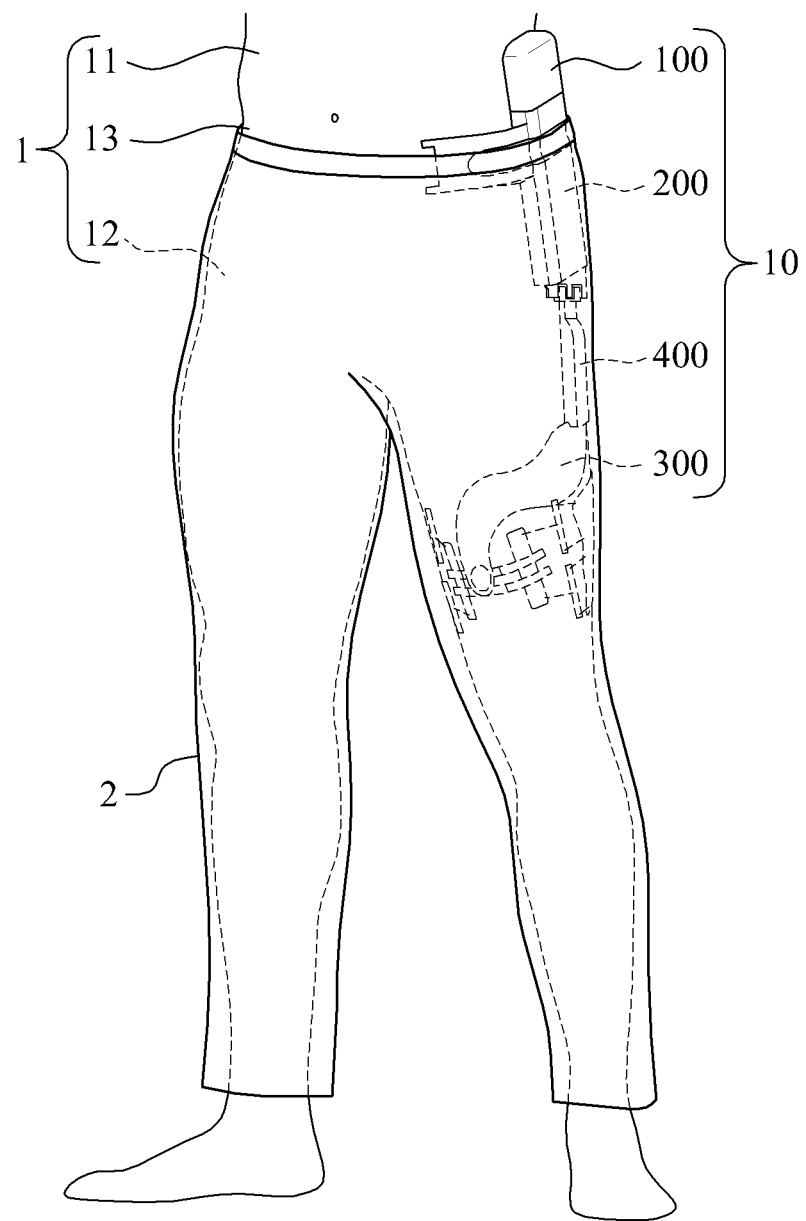
FIG. 6 illustrates a motion assistance apparatus including a case disposed on an object according to some example embodiments.

FIG. 5 illustrates the motion assistance apparatus 10 including a case 260. FIG. 6 illustrates the motion assistance apparatus 10 including the case 260 disposed on the object 1.

Referring to FIGS. 5 and 6, the driving module 200 may further include the case 260. The case 260 may be provided to cover at least a portion of the driving module 200. The case 260 may prevent direct contact between internal components of the motion assistance apparatus 10 and skin of a human, thereby increasing wearability.

The case 260 may prevent an external exposure of at least a portion of the power transmitting member 230. A user may hold a portion of clothes 2 on an outer surface of the case 260. For example, a waistband of pants may be held. Thus, the power transmitting member 230 may prevent the power transmitting member 230 from being restrained by the waistband of the clothes 2. Thus, the power transmitting member 230 may smoothly transmit power. The case 260 may enable the object 1 to wear the clothes 2 over the motion assistance apparatus 10.

The case 260 may include a first holding portion 262 to hold the clothes 2. For example, the first holding portion 262 may be formed to be depressed from the outer surface of the case 260. The first holding portion 262 may prevent the clothes 2 from sliding down by stably holding a portion of the clothes 2.

Similarly, when the object fix member 210 is fixed on a waist of a human, the object fix member 210 may include a second holding portion 212 to hold the clothes 2. The second holding portion 212 may be formed to be depressed from an outer surface of the object fix member 210. The second holding portion 212 may prevent the clothes 2 from sliding down by stably holding a portion of the clothes 2. The second holding portion 212 may be formed in succession to the first holding portion 262.

The power providing module described above may include the actuator module 100 and the first sub-module 220.

The power applying module described above may include the second rotating member 246, the axis of rotation 248, the connection axis 249, the supporting module 300, and the connection module 400.

Figure 7:
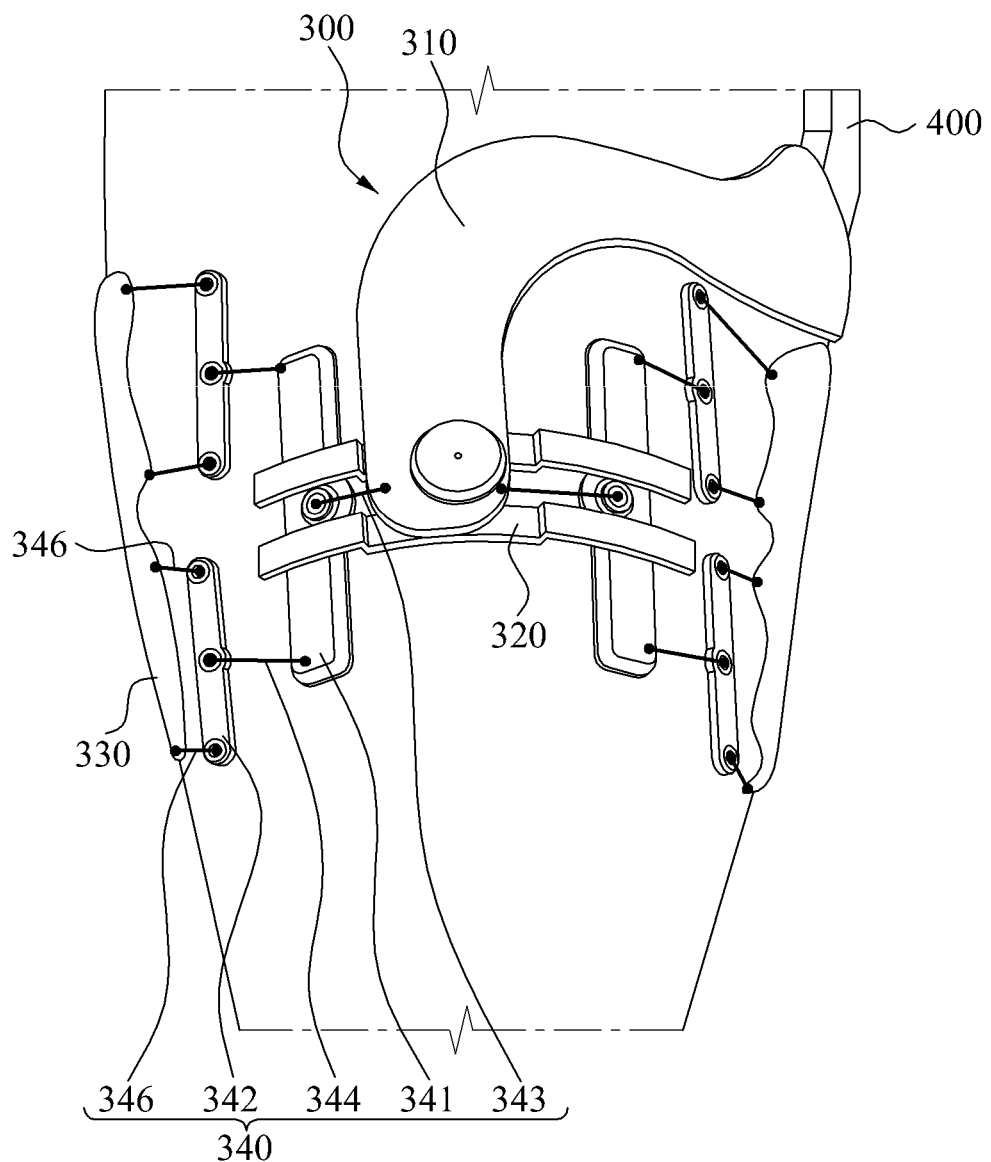
FIG. 7 illustrates a supporting module according to some example embodiments.

FIG. 7 illustrates the supporting module 300.

Referring to FIG. 7, the supporting module 300 may support an action part of the object 1. The action part refers to a part in contact with the supporting module 300 to receive a force directly from the supporting module 300.

The supporting module 300 may move using power received from the connection module 400. When the supporting module 300 moves, the action part of the object 1 supported by the supporting module 300 may move. The supporting module 300 may move the action part of the object 1 by pushing or pulling the action part of the object 1.

When the first rotating member 226 of FIG. 3 rotates, the second rotating member 246 may rotate in a direction corresponding to a direction of rotation of the first rotating member 226. Based on the direction of rotation of the second rotating member 246, the supporting module 300 may push or pull the action part of the object 1.

For example, the supporting module 300 may move a thigh of a human. Referring to FIG. 3, when the first rotating member 226 rotates in a clockwise direction, the second rotating member 246 may rotate in the clockwise direction, and the supporting module 300 may rotate in a forward direction of the human. In some example embodiments, the supporting module 300 may pull the thigh of the human to move forward.

Conversely, when the first rotating member 226 rotates in a counterclockwise direction, the second rotating member 246 may rotate in the counterclockwise direction, and the supporting module 300 may rotate in a backward direction of the human. In some example embodiments, the supporting module 300 may push the thigh of the human to move backward.

The direction of rotation and the direction of movement may be changed based on a connection relationship among the first rotating member 226, the second rotating member 246, and the supporting module 300.

The supporting module 300 may include a supporting frame 310, a pressure member 320, a supporting member 330, and a dispersion member 340.

The supporting frame 310 may extend from the connection module 400. The supporting frame 310 may push or pull the action part of the object 1. The supporting frame 310 may be provided to cover at least a portion of the action part of the object 1.

The supporting frame 310 may include a portion to be disposed on a front surface or a rear surface of the action part of the object 1. The supporting frame 310 may include a surface parallel to an axial direction of the connection module 400. The supporting frame 310 may include a surface perpendicular to a trajectory of rotation of the connection module 400.

For example, referring to FIG. 7, the supporting frame 310 may extend forward from the connection module 400. The extending portion may be disposed on a front surface of the thigh of the human.

The supporting frame 310 may include a curved surface corresponding to a shape of the action part of the object 1. The supporting frame 310 may have a curved cross-section.

The pressure member 320 may apply pressure to one side of the action part of the object 1. The pressure member 320 may apply pressure to the action part when the supporting frame 310 moves toward the action part. The pressure member 320 may be connected to the supporting frame 310. The pressure member 320 may be fixed to the supporting frame 310. The pressure member 320 may be provided to be integrated with the supporting frame 310.

The pressure member 320 may be pressurized by the supporting frame 310 to apply pressure to the action part of the object 1. The pressure member 320 may be disposed along a perimeter of the action part of the object 1. The pressure member 320 may extend to both sides based on the supporting frame 310. The pressure member 320 may include a curved surface corresponding to the action part of the object 1.

The supporting member 330 may support another side of the action part of the object 1. The supporting member 330 may pull the action part when the supporting frame 310 moves away from the action part. The supporting member 330 may be disposed on an opposite side of the pressure member 320 based on the action part of the object 1.

The supporting member 330 may be disposed along the perimeter of the action part of the object 1. The supporting member 330 may be formed using a flexible material. For example, the supporting member 330 may include fabric, sponge, and sheet. The supporting member 330 may be provided in a form of a thin plate having a desired width (that may or may not be predetermined).

As described above, the pressure member 320 and the supporting member 330 may be disposed on the front surface and the rear surface of the action part of the object, respectively. However, the pressure member 320 may be disposed on the rear surface of the action part of the object 1, and the supporting member 330 may be disposed on the front surface of the action part of the object 1.

The dispersion member 340 may connect the pressure member 320 to the supporting member 330. The dispersion member 340 may disperse a tensile force by the pressure member 320 in a longitudinal direction of the action part of the object 1.

The dispersion member 340 may include a first dispersion piece 341, a second dispersion piece 342, a first connection portion 343, a second connection portion 344, and a third connection portion 346.

The first dispersion piece 341 and the second dispersion piece 342 may be collectively referred to as a "dispersion piece". The first connection portion 343, the second connection portion 344, and the third connection portion 346 may be collectively referred to as a "connection portion".

The dispersion piece and the connection portion may have different rigidities. For example, the dispersion piece may have a higher rigidity than the connection portion. In detail, the dispersion piece may include a rigid material, for example, a metal, a plastic, and a ceramic. The connection portion may include a flexible material, for example, a metallic cable, a metallic wire, a spring, a fabric string, a fabric plate, a rubber band, and a rubber plate.

However, the material of the dispersion piece is not limited to a rigid substance. For example, the dispersion piece may include a flexible material having a higher rigidity than the connection portion. The dispersion piece and the connection portion may have identical rigidities.

The first dispersion piece 341 may be connected to the pressure member 320, and disposed in a direction intersecting a direction of the perimeter of the action part of the object 1. For example, the first dispersion piece 341 may be disposed in a direction perpendicular to the direction of the perimeter of the action part of the object 1.

The first dispersion piece 341 may be connected to the supporting frame 310 by a single first connection portion 343, and connected to the second dispersion piece 342 by two second connection portions 344.

The first connection portion 343 may connect the first dispersion piece 341 to the supporting frame 310 to be movable with respect to the supporting frame 310. The first dispersion piece 341 may be connected movably and/or rotatably to the supporting frame 310. The first connection portion 343 may connect the first dispersion piece 341 to the supporting frame 310 to be freely movable with respect to the supporting frame 310 within a desired radius (that may or may not be predetermined). The first connection portion 343 may prevent the first dispersion piece 341 from being spaced from the supporting frame 310 outside the desired radius (that may or may not be predetermined).

A length of the first connection portion 343 may be shorter than a length of the first dispersion piece 341. For example, the length of the first connection portion 343 may be shorter than or equal to half of the length of the first dispersion piece 341.

One side of the first connection portion 343 may be connected to a midpoint of the longitudinal direction of the first dispersion piece 341.

The first dispersion piece 341 may also be connected movably to the pressure member 320, similar to the supporting frame 310. Detailed descriptions thereon will be omitted herein.

The two second connection portions 344 may be connected to one end and another end of the first dispersion piece 341, respectively. The two second connection portions 344 may also be connected to two second dispersion pieces 342, respectively.

A single first connection portion 343 may be connected to one side of the first dispersion piece 341, and two second connection portions 344 may be connected to another side of the first dispersion piece 341. The first connection portion 343 and the second connection portions 344 may be disposed in opposite directions.

In the foregoing structure, a tensile force applied to the first connection portion 343 may be divided and applied to the two second connection portions 344. The tensile force applied to one point of the first dispersion piece 341 may be dispersed to two points.

The first dispersion piece 341 may be disposed between the pressure member 320 and the action part of the object 1. In some example embodiments, the first dispersion piece 341 may be pressurized by the pressure member 320 and, consequently, may apply pressure to the action part of the object 1. The first dispersion piece 341 may increase a pressurization area.

The second dispersion piece 342 may be connected to the first dispersion piece 341 and the supporting member 330. The second dispersion piece 342 may be disposed in a direction intersecting a perimeter direction of the action part of the object 1. For example, the second dispersion piece 342 may be disposed in a direction perpendicular to the perimeter direction of the action part of the object 1.

The second dispersion piece 342 may be connected to the first dispersion piece 341 by a single second connection portion 344, and connected to the supporting member 330 by two third connection portions 346.

The second connection portion 344 may connect the second dispersion piece 342 to the first dispersion piece 341 to be movable with respect to the first dispersion piece 341. The second dispersion piece 342 may be connected movably and rotatably to the first dispersion piece 341. The second connection portion 344 may be connected freely movable within a desired radius (that may or may not be predetermined) with respect to the first dispersion piece 341. The second connection portion 344 may prevent the second dispersion piece 342 from being spaced apart from the first dispersion piece 341 outside the desired radius (that may or may not be predetermined).

A length of the second connection portion 344 may be shorter than a length of the second dispersion piece 342. For example, the length of the second connection portion 344 may be shorter than or equal to half of the length of the second dispersion piece 342.

One side of the second connection portion 344 may be connected to a midpoint of the longitudinal direction of the second dispersion piece 342.

The two third connection portions 346 may be connected to one end and another end of the second dispersion piece 342, respectively. The two third connection portions 346 may also be connected to two points of the supporting member 330, respectively.

A single second connection portion 344 may be connected to one side of the second dispersion piece 342, and two third connection portions 346 may be connected to another end of the second dispersion piece 342. The second connection portion 344 and the third connection portions 346 may be disposed in opposite directions.

In the foregoing structure, a tensile force applied to the second connection portion 344 may be divided and applied to the two third connection portions 346. The tensile force concentrated on a single point of the second dispersion piece 342 may be dispersed to two points.

Thus, the tensile force applied to the first connection portion 343 may be divided and applied to four third connection portions 346. The tensile force produced by the movement of the pressure member 320 may be dispersed in a direction perpendicular to the perimeter direction of the action part of the object 1 through the first dispersion piece 341 and the second dispersion piece 342.

Although FIG. 7 illustrates a case in which the dispersion member 340 is provided in a double structure of the first dispersion piece 341 and the second dispersion piece 342, a triple or more structure may also be provided by interposing an additional dispersion piece between the second dispersion piece 342 and the supporting member 330. In addition, a single structure may also be provided by omitting the second dispersion piece 342. The two second connection portions 344 connected to the first dispersion piece 341 may be connected to two different points of the supporting member 330.

Figure 8A:
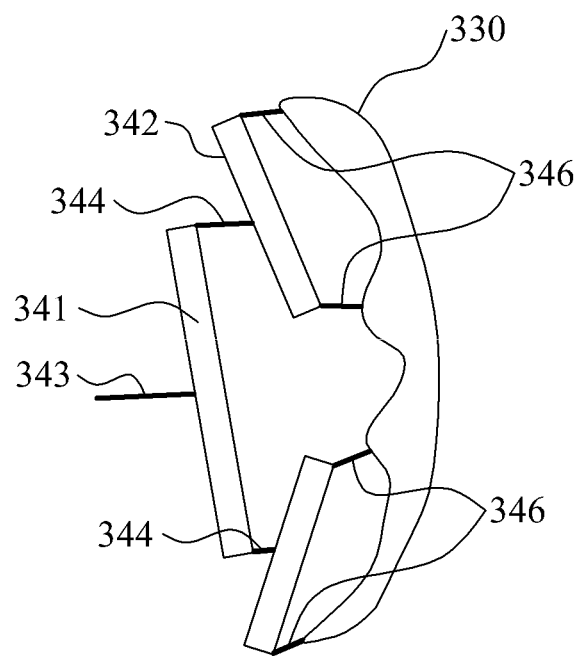
FIGS. 8A and 8B illustrate various operating states of a dispersion member according to some example embodiments.
Figure 8B:
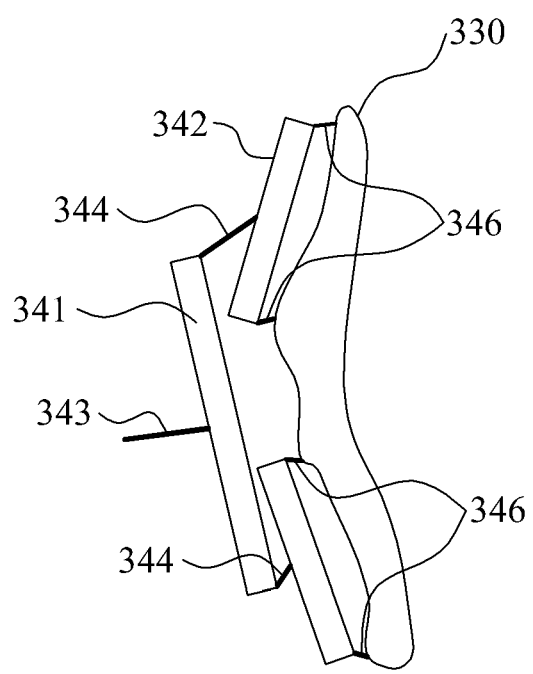

FIGS. 8A and 8B illustrate various operating states of the dispersion member 340.

Referring to FIGS. 8A and 8B, the dispersion member 340 may be provided in various forms to disperse a force. Angles of the first dispersion piece 341 and the second dispersion piece 342 may be adjusted based on a motion pattern or a shape of the action part of the object 1.

FIG. 8A illustrates a case in which an intermediate portion of the action part of the object 1 covered by the supporting member 330 is more transformed. In some example embodiments, the two second dispersion pieces 342 may be adjusted to tilt toward the intermediate portion of the supporting member 330 based on a magnitude of a load. In so doing, distance from the second dispersion pieces 342 to the supporting member 330 may be equalized and, thus, tensile forces applied to the four third connection portions 346 may be equalized. Accordingly, based on FIG. 8A, a distribution of a force vertically applied to the supporting member 330 may be equalized.

FIG. 8B illustrates a case in which an upper portion and a lower portion of the action part of the object 1 covered by the supporting member 330 are transformed to a greater degree. In some example embodiments, the two second dispersion pieces 342 may be adjusted to tilt toward an opposite side of the intermediate portion of the supporting member 330 based on a magnitude of a load. In so doing, distances from the second dispersion pieces 342 to the supporting member 330 may be equalized and, thus, tensile forces applied to the four third connection portions 346 may be equalized. Accordingly, based on FIG. 8B, a distribution of a force vertically applied to the supporting member 330 may be equalized.

As illustrated in FIGS. 8A and 8B, the first dispersion piece 341 and the second dispersion piece 342 may be freely rotatable and/or movable within a desired radius (that may or may not be predetermined). Thus, although a desired portion (that may or may not be predetermined) of the action part is more transformed, a load concentration on the corresponding portion may be prevented and a force may be distributed evenly.

Figure 9A:
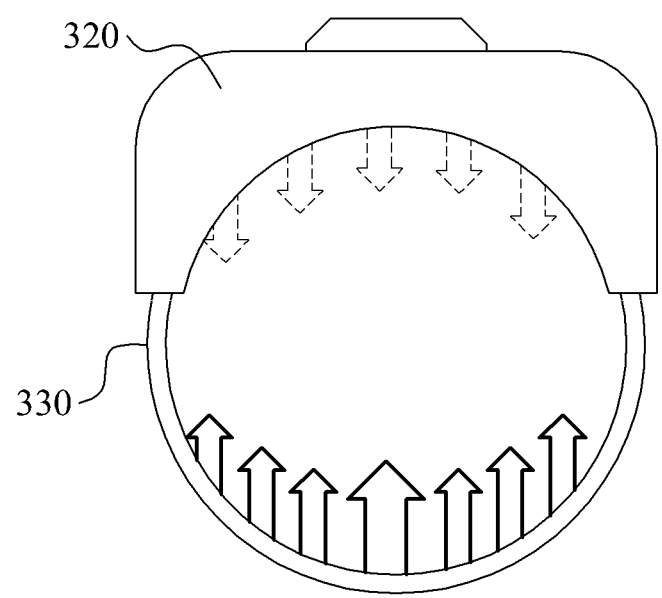
FIGS. 9A and 9B illustrate a distribution of a force applied to a supporting module according to some example embodiments.
Figure 9B:
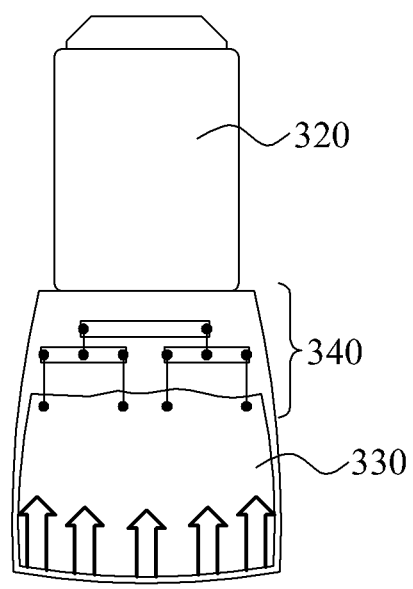

FIGS. 9A and 9B illustrate a distribution of a force applied to the supporting member 330. In detail, FIG. 9A illustrates the supporting member 330 viewed from above, and FIG. 9B illustrates the supporting member 330 viewed from the side.

Hereinafter, descriptions will be provided with reference to FIG. 9A.

In FIG. 9A, arrows indicated with a solid line illustrate a distribution of a force applied to the action part of the object 1 when the supporting member 330 pulls the action part of the object 1.

The pressure member 320 may be disposed broadly over a front surface of the action part of the object 1, and the supporting member 330 may be connected to both sides of the pressure member 320. In some example embodiments, a force used for the pressure member 320 to pull the supporting member 330 may be applied frontward. Thus, an efficiency of force transmission may increase. In addition, a distance between supporting points of the supporting member 330 may be maximized and, thus, a distance from the action part of the object 1 may decrease.

In FIG. 9A, arrows indicated with a broken line illustrate a distribution of a force applied to the action part of the object 1 when the pressure member 320 pushes the action part of the object 1.

The pressure member 320 may be disposed in a direction perpendicular to a movement direction of the action part of the object 1. The pressure member 320 may be disposed on the front surface of the action part of the object 1. The pressure member 320 may be formed using a rigid material. In some example embodiments, a pressure applied by the pressure member 320 to the action part of the object 1 may be equalized.

Hereinafter, descriptions will be provided with reference to FIG. 9B.

FIG. 9B illustrates an example of equalizing a pressure applied from the supporting member 330 to the action part of the object 1, when viewed from the side, using a double dispersion structure of the dispersion member 340. In the double dispersion structure, tensile forces applied to the supporting member 330 may be approximately parallel. Thus, the supporting member 330 may stably pull the action part of the object 1 using a relatively broad supporting surface, rather than being folded.

Figure 10:
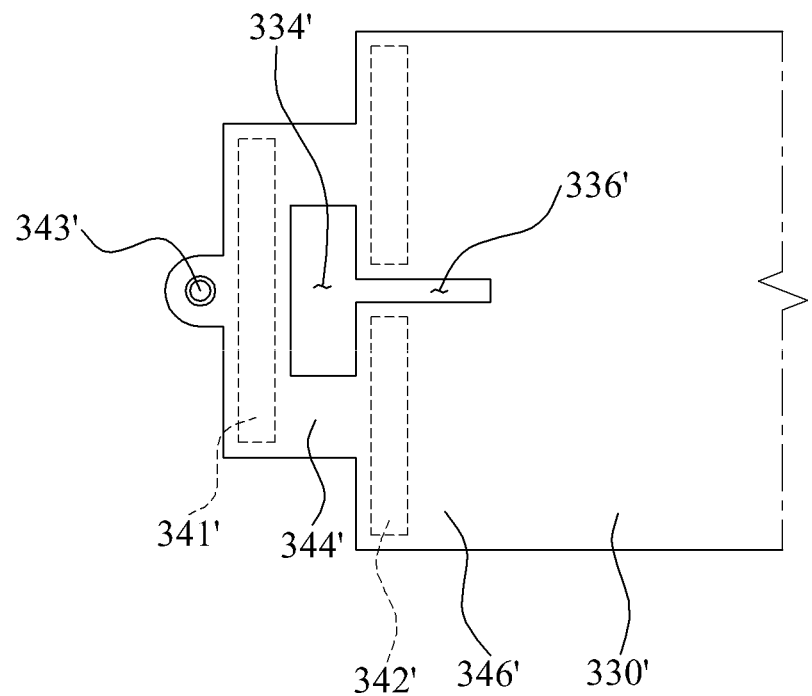
FIG. 10 illustrates a supporting member according to some example embodiments.

FIG. 10 illustrates a supporting member 330' according to some example embodiments.

Hereinafter, the same name may be used to describe an element included in the example embodiments described above and an element having a common function. Unless otherwise mentioned, the descriptions on the example embodiments may be applicable to the following example embodiments and, thus, duplicated descriptions will be omitted for conciseness.

Referring to FIG. 10, the supporting member 330' may include a first connection portion 343', a separation hole 334', and a separation recess 336'.

The first connection portion 343' may be connected to the pressure member 320 of FIG. 7.

The separation hole 334' may be provided on one side of the supporting member 330'. A first dispersion piece 341' may be disposed on one side of the separation hole 334'. The first dispersion piece 341' may be disposed in a direction parallel to a longitudinal direction of the separation hole 334'.

The first dispersion piece 341' may be disposed on the one side of the supporting member 330'. The first dispersion piece 341' may be disposed between the first connection portion 343' and the separation hole 334'. The first connection portion 343' may be disposed at a midpoint of the first dispersion piece 341'.

In some example embodiments, the first dispersion piece 341' may be inserted into an internal portion of the supporting member 330'. The supporting member 330' may include two planes, and the first dispersion piece 341' may be interposed between the two planes. Between the two planes, at least a portion of one plane corresponding to a perimeter of the first dispersion piece 341' may be bonded to prevent a separation of the first dispersion piece 341'. In some example embodiments, at least a portion of the supporting member 330' may be stitched along the perimeter of the first dispersion piece 341'. In some example embodiments, the first dispersion piece 341' may be fixed on an outer surface of the supporting member 330'.

In some example embodiments, the first dispersion piece 341' may be fixed on an outer surface of the supporting member 330'.

The separation recess 336' may be formed to be depressed on another side of the separation hole 334'. The separation recess 336' may be disposed on an opposite side of the first dispersion piece 341' based on the separation hole 334'. Second dispersion pieces 342' may be disposed on an upper side and a lower side of the separation hole 334', respectively.

The second dispersion pieces 342' may be disposed in a direction intersecting a longitudinal direction of the separation recess 336'. The second dispersion pieces 342' may be disposed in a direction orthogonal to the longitudinal direction of the separation recess 336'. The second dispersion pieces 342' may be disposed to be parallel to the first dispersion piece 341'.

Perimeters of the second dispersion pieces 342' may be fixed while the second dispersion pieces 342' is inserted into the internal portion of the supporting member 330'. The second dispersion pieces 342' may be fixed on the outer surface of the supporting member 330'. The second dispersion pieces 342' may be disposed in a similar manner in which the first dispersion piece 341' is disposed and, thus, duplicated descriptions will be omitted for conciseness.

A portion of the supporting member 330' disposed between the first dispersion piece 341' and the second dispersion pieces 342' may be referred to as a second connection portion 344'. The second connection portion 344' may correspond to a portion corresponding to the upper side and the lower side of the separation hole 334'.

A portion of the supporting member 330' corresponding to an upper side and a lower side of the separation recess 336' may be referred to as a third connection portion 346'.

The separation recess 336' may include a first separation recess disposed between the two second dispersion pieces 342', and a second separation recess to be depressed further from the first separation recess. The second separation recess may be formed to be depressed to an opposite side of the separation hole 334' based on the first separation recess.

As described above, a supporting member and a dispersion member may be provided to be integrated.

Figure 11:
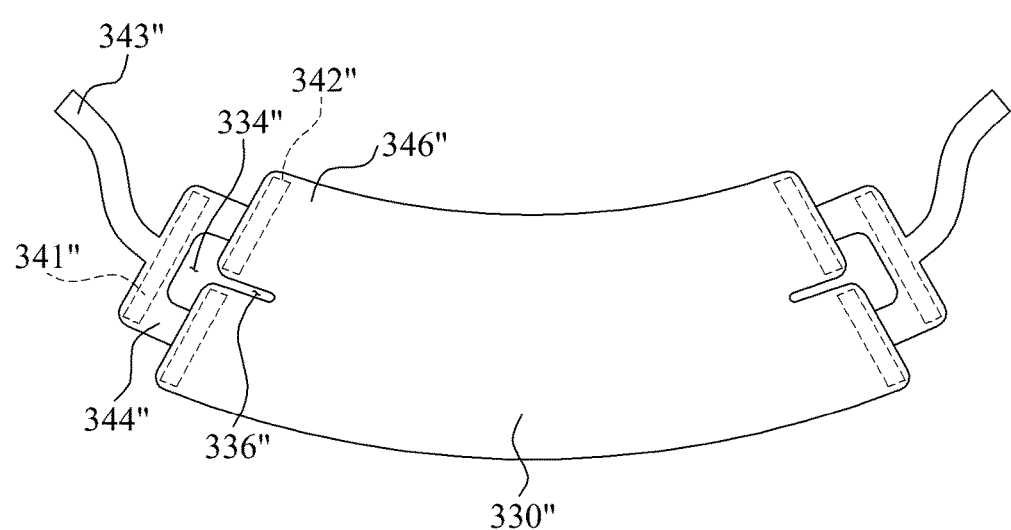
FIG. 11 illustrates a supporting member according to some example embodiments.

FIG. 11 illustrates a supporting member 330" according to some example embodiments.

Referring to FIG. 11, the supporting member 330" may include a first connection portion 343", a separation hole 334", and a separation recess 336".

A first dispersion piece 341" may be disposed between the first connection portion 343" and the separation hole 334".

Second dispersion pieces 342" may be disposed on an upper side and a lower side of the separation recess 336".

A portion connecting the first dispersion piece 341" to the second dispersion pieces 342" may be referred to as a second connection portion 344".

A portion of the supporting member 330" disposed on the upper side and the lower side of the separation recess 336" may be referred to as a third connection portion 346".

The supporting member 330" may be formed to have an upper edge and a lower edge differing in length. The upper edge and the lower edge may be provided in a form of being curved in identical directions. The supporting member 330" may be provided in a form of an unfolded side surface of a truncated cone.

In the foregoing structure, the supporting member 330" may be in close contact with a portion having a thickness varying from one side to another side in the action part of the object 1, whereby wearability may increase and a space between the supporting member 330" and the object 1 may be minimized.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to muscular strength assisting apparatuses, those skilled in the art will appreciate that some example embodiments may be applied to other types of systems, such as systems not used in the medical field (e.g., aerospace teleoperation systems, apparatuses for handling hazardous materials, patrol apparatuses, military apparatuses), humanoid apparatuses, or more general purpose control systems. Those skilled in the art will appreciate that the muscular strength assisting apparatuses described in this application have a myriad of practical uses.

Some example embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A driving module, comprising:
   an object fix member configured to be fixed to an object;
   a first sub-module including a body portion and a first rotating member, the body portion connected to a first side of the object fix member, the first rotating member connected rotatably to the body portion;
   a second sub-module including an extension link and a second rotating member, the extension link connected to a second side of the object fix member, the second rotating member connected rotatably to the extension link; and
   a power transmitting member connected to the first rotating member and the second rotating member, the power transmitting member configured to transmit power,
   wherein the first sub-module and the second sub-module are disposed on opposite sides of the object fix member and spaced apart from each other by the object fix member.

2. The driving module of claim 1, wherein the first sub-module further comprises:
   a pivot between the body portion and the object fix member, the pivot configured to connect the body portion movably to the object fix member.

3. The driving module of claim 2, wherein the pivot comprises a pivot axis and the pivot is configured to enable the body portion to rotate with respect to the object fix member about the pivot axis.

4. The driving module of claim 3, further comprising:
a restoring spring on a first side of the pivot, the restoring spring configured to return the body portion to a standard position when an external force applied to the body portion is removed.

5. The driving module of claim 3, wherein an axis of rotation of the second rotating member is orthogonal to the pivot axis of the pivot.

6. The driving module of claim 3, wherein the power transmitting member is in a direction orthogonal to an axis of rotation of the first rotating member.

7. The driving module of claim 2, wherein the pivot comprises flexible material having elasticity.

8. The driving module of claim 1, wherein a first side of the extension link is connected to the object fix member,
wherein a second side of the extension link is configured to extend to a joint part of the object, and
wherein the second rotating member is on the second side of the extension link.

9. The driving module of claim 1, wherein the power transmitting member comprises a flat spring.

10. The driving module of claim 1, wherein the power transmitting member comprises:
a first power transmitting member configured to connect a first side of the first rotating member to a first side of the second rotating member; and
a second power transmitting member configured to connect a second side of the first rotating member to a second side of the second rotating member,
wherein the first and second sides of the first rotating member are on opposite sides based on an axis of rotation of the first rotating member, and
wherein the first and second sides of the second rotating member are on opposite sides based on an axis of rotation of the second rotating member.

11. The driving module of claim 1, wherein the second sub-module further comprises:
a connection axis on a first side of the second rotating member and an axis of rotation of the second rotating member which is orthogonal to the connection axis.

12. The driving module of claim 1, further comprising:
a case configured to prevent external exposure of at least a portion of the power transmitting member.

13. The driving module of claim 12, wherein the case comprises a holding portion configured to hold clothes.

14. A motion assistance apparatus, comprising:
an actuator configured to provide power;
an object fix member configured to be fixed to an object;
a driving module including a first sub-module configured to receive the power from the actuator, a second sub-module configured to receive the power from the actuator by way of the first sub-module, and a power transmitting member configured to transmit power between the first sub-module and the second sub-module; and
a supporting module connected to the second sub-module and configured to support and move a part of the object,
wherein the second sub-module is configured to be on a first side of a joint part and the second sub-module is configured to be connected to the part of the object,
the first sub-module is spaced away from the joint part, and
the first sub-module and the second sub-module are disposed on opposite sides of the object fix member and spaced apart from each other by the object fix member.

15. The motion assistance apparatus of claim 14, further comprising:
a connection module between the driving module and the supporting module;
wherein the connection module comprises:
a first connection link; and
a second connection link connected movably to the first connection link, and configured to adjust an overall length of the connection module.

16. A motion assistance apparatus, comprising:
a power providing module configured to generate power;
an object fix member configured to be fixed to an object;
a power applying module including a rotating member configured to be on a first side of a joint part of the object and a supporting module connected to the rotating member, the rotating member configured to supplement to or substitute for a function of the joint part, the supporting module configured to support a portion of the object that is connected to the joint part;
a power transmitting member configured to transmit the power from the power providing module to the rotating member; and
a case configured to cover at least a portion of the power transmitting member,
wherein the power providing module and the power applying module are disposed on opposite sides of the object fix member and spaced apart from each other by the power transmitting member.

17. The motion assistance apparatus of claim 16, wherein the rotating member is configured to be on a first side of a hip joint of the object,
wherein the supporting module is configured to support a lower body of the object,
wherein the power providing module is configured to be on an upper body of the object, and
wherein the case is configured to be on a waist of the object.

* * * * *